United States Patent [19]

Meilland

[11] Patent Number: Plant 6,088

[45] Date of Patent: Jan. 26, 1988

[54] ROSE-PLANT—MEICOUBLAN VARIETY

[75] Inventor: Marie-Louise Meilland, Antibes, France

[73] Assignee: The Conard-Pyle Company, West Grove, Pa.

[21] Appl. No.: 768,360

[22] Filed: Aug. 22, 1985

[51] Int. Cl.[4] ..... A01H 5/00

[52] U.S. Cl. ..... Plt./1

[58] Field of Search ..... Plt./1, 23

*Primary Examiner*—Robert E. Bagwill

*Attorney, Agent, or Firm*—Burns, Doane, Swecker & Mathis

[57] ABSTRACT

A new and distinct variety of rose plant is provided which forms in abundance attractive very double, generally white blossoms. The plant exhibits a spreading growth habit which renders it highly suited for use as a ground cover. Good cold hardiness and resistance to fungal diseases are manifest. The new variety can be readily propagated from cuttings.

15 Drawing Figures

SUMMARY OF THE INVENTION

The new variety of ground cover rose plant was created by artificial pollination wherein two parents were crossed which previously had been studied in the hope that they would contribute the desired characteristics. The female parent (i.e., the seed parent) of the new variety was the variety Temple Bells. The male parent (i.e., the pollen parent) of the new variety was the variety Meigurami. The parents of the new variety are non-patented in the United States. The parentage of the new variety can be summarized as follows:

Temple Bells × Meigurami.

The seeds resulting from the above pollination were sown in a greenhouse and 10 plantlets were obtained which were physically and biologically different from each other. Selective study resulted in the identification of a single plant of the new variety.

It was found that the new variety of ground cover rose plant of the present invention possesses the following combination of characteristics:

(a) forms in abundance attractive, relatively large, fully double blossoms which generally are white in coloration,
(b) forms dark glossy foliage,
(c) exhibits a spreading growth habit which forms a plant having a greater width than height,
(d) exhibits good cold hardiness, and
(e) exhibits good resistance to fungal diseases.

The large white flowers tend to form on wood which is one or two years old.

The new variety meets the needs of the horticultural industry for many usages. It is particularly well-suited when grown en masse for use as an attractive, dense, and low-growing ornamental ground cover in parks, gardens, and residential and commercial landscapes. The dark glossy leaves in combination with the white flowers provide a strikingly noteworthy appearance.

The new variety has been found to undergo asexual propagation by a number of routes, including budding, grafting, use of cuttings, etc. The new variety propagates well from cuttings and readily forms its own roots. Accordingly, such propagation can be carried out on an inexpensive basis. The characteristics of the new variety have been found to be strictly transmissible by such asexual propagation from one generation to another.

The new variety has been named the Meicoublan Variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were grown outdoors at LeLuc, France.

FIG. 1 illustrates a specimen of a young shoot;

FIGS. 2/3 illustrate a cluster of floral buds before the opening of the sepals;

DETAILED DESCRIPTION

Figures 1, 2, 3, 4, 5, 6, 7, 8, 9, 10, 11, 12, 13, 14, 15:
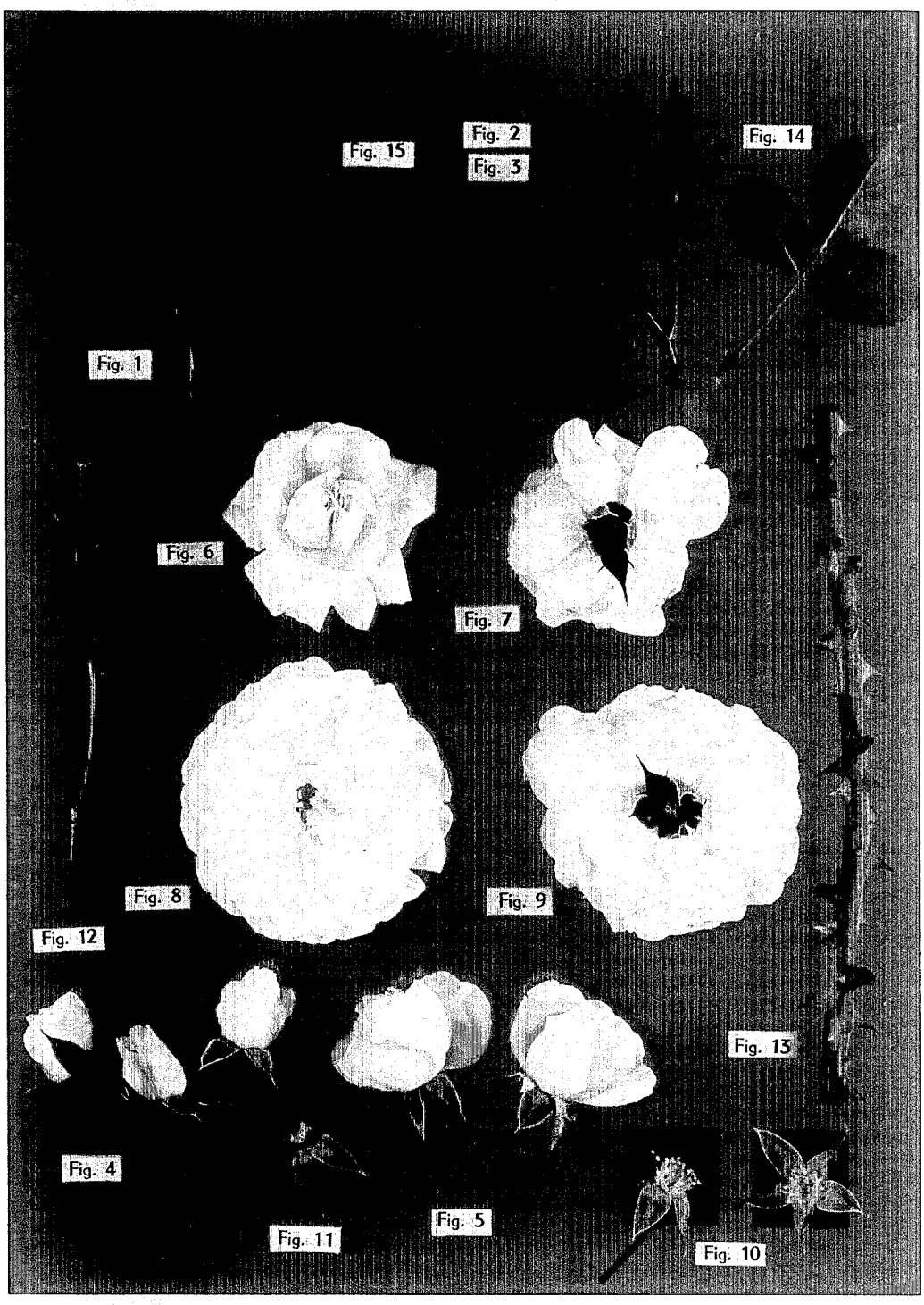
FIG. 4 illustrates specimens of three floral buds at the opening of the petals.
FIG. 5 illustrates specimens of two flowers in the course of opening.
FIG. 6 illustrates a specimen of a partially open flower - plan view - obverse.
FIG. 7 illustrates a specimen of a partially open flower - plan view - reverse.
FIG. 8 illustrates a specimen of a fully open flower - plan view - obverse.
FIG. 9 illustrates a specimen of a fully open flower - plan view - reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets - under surface.
FIG. 15 illustrates a specimen of a leaf with five leaflets - upper surface.

The chart used in the identification of the colors is that of The Royal Horticultural Society (R.H.S. Colour Chart). The description is based on three-year old specimens of the new variety during June while growing outdoors on their own roots in field soil at LeLuc, France.

Class: Ground cover.

Plant:

*Height.*—Approximately 90 to 140 cm.

*Habit.*—Spreading growth habit which forms a plant having a greater width than height.

Branches:

*Color.*—Young stems: Yellow-Green Group 146C somewhat suffused with reddish brown. Adult wood: Yellow-Green Group 146B.

Leaves:

*Petioles.*—Upper surface: grooved and reddish brown on young foliage and light green on adult foliage. Under surface: light green with several small hooks.

*Leaflets.*—Number: 3,5, and 7 (most often). Shape: elliptic to ovate. Serration: simple and regular. General appearance: dark and glossy. Color (young foliage): Upper surface: green with bronze shading. Under surface: reddish bronze. Color (adult foliage): Upper surface: Yellow-Green Group 147A. Under surface: Yellow-Green Group 147B.

Inflorescence:

*Number of flowers.*—Approximately 2 to 14 per stem.

*Peduncle.*—Its length is approximately 2 cm. on average.

*Buds.*—Shape: oval. Color upon opening: Upper surface: White Group 155A. Under surface: White Group 155A often with a slight pink tinge at the petal margins.

*Flower.*—Diameter: approximately 8 cm. on average. Color (when opening begins): Upper surface: White Group 155A. Under surface: White Group 155A often with a slight pink tinge at the petal margins. Color (when partially open): Upper surface: White Group 155A often bordered with pale pink and suffused with Yellow Group 11D. Under surface: White Group 155A with hint of pink on petal margins. Color (at end of opening): Upper surface: White Group 155A and very lightly bordered with pale pink and somewhat suffused with Yellow Group 11D. Under surface: White Group 155A with a light pink tinge on the petal margins. Fragrance: none. Lasting quality: long. Petal number: approximately 60 to 70. Petal form: ovate to broadly cordate. Stamen number: approximately 90 on average. Pistils: approximately 38 on average.

Development:

*Hardiness.*—Very good.

*Disease resistance.*—Extremely resistant to the major fungal diseases which commonly attack roses.

I claim:

1. A new and distinct variety of ground cover rose plant characterized by the following combination of characteristics:

(a) forms in abundance attractive, fully double blossoms which are generally white in coloration, (b) forms dark glossy foliage, (c) exhibits a spreading growth habit which forms a plant having a greater width than height, (d) exhibits good cold hardiness, and (e) exhibits good resistance to fungal diseases;

substantially as herein shown and described.

* * * * *